United States Patent
Nord et al.

(10) Patent No.: US 9,907,979 B2
(45) Date of Patent: Mar. 6, 2018

(54) APPARATUS AND METHOD TO FACILITATE ADAPTING A RADIATION TREATMENT PLAN

(75) Inventors: Janne Nord, Espoo (FI); Jarkko Peltola, Tuusula (FI)

(73) Assignee: Varian Medical Systems International AG, Cham (CH)

(*) Notice: Subject to any disclaimer, the term of this patent is extended or adjusted under 35 U.S.C. 154(b) by 197 days.

(21) Appl. No.: 12/207,265

(22) Filed: Sep. 9, 2008

(65) Prior Publication Data
US 2010/0061510 A1    Mar. 11, 2010

(51) Int. Cl.
A61N 5/10    (2006.01)

(52) U.S. Cl.
CPC ............ *A61N 5/103* (2013.01); *A61N 5/1031* (2013.01)

(58) Field of Classification Search
USPC ......................................................... 378/65
See application file for complete search history.

(56) References Cited

U.S. PATENT DOCUMENTS

| | | | |
|---|---|---|---|
| 5,602,892 A | 2/1997 | Llacer | |
| 5,782,739 A | 7/1998 | Criss et al. | |
| 6,038,283 A | 3/2000 | Carol et al. | |
| 6,260,005 B1 | 7/2001 | Yang et al. | |
| 6,411,675 B1 | 6/2002 | Llacer | |
| 6,560,311 B1 | 5/2003 | Shepard et al. | |
| 6,661,870 B2 | 12/2003 | Kapatoes et al. | |
| 6,882,702 B2 | 4/2005 | Luo | |
| 7,162,008 B2 | 1/2007 | Earl et al. | |
| 7,180,980 B2 | 2/2007 | Nguyen | |
| 7,333,591 B2 | 2/2008 | Earl et al. | |
| 2003/0048868 A1 | 3/2003 | Bailey et al. | |
| 2005/0111621 A1* | 5/2005 | Riker et al. | 378/65 |
| 2006/0078086 A1 | 4/2006 | Riley et al. | |
| 2006/0256915 A1 | 11/2006 | Otto et al. | |
| 2008/0049896 A1* | 2/2008 | Kuduvalli | 378/65 |

(Continued)

FOREIGN PATENT DOCUMENTS

| | | |
|---|---|---|
| WO | 2003076003 A2 | 9/2003 |
| WO | 2005035061 A2 | 4/2005 |

(Continued)

OTHER PUBLICATIONS

Yi et al., "A Dose Rate Modulated Tracking Radiation Therapy System and Method," U.S. Appl. No. 60/874,678; filed Dec. 14, 2006; 23 pages.

(Continued)

*Primary Examiner* — Hoon Song
(74) *Attorney, Agent, or Firm* — Fitch, Even, Tabin & Flannery LLP

(57) ABSTRACT

An existing radiation treatment plan is accessed for a given patient as well as first information (such as automatically generated updated information) regarding at least one physical characteristic as corresponds to the radiation treatment of this patient. One then initiates, prior to receiving second information (such as user input) regarding the first information, an automatic adaptation process to adapt the treatment plan to accommodate the first information. Upon later receiving second information regarding the first information, one then modifies the automatic adaptation process itself to incorporate the second information regarding the first information.

25 Claims, 1 Drawing Sheet

(56) References Cited

U.S. PATENT DOCUMENTS

2008/0144772 A1* 6/2008 Yi et al. .................... 378/65
2008/0226030 A1   9/2008 Otto
2008/0298550 A1  12/2008 Otto

FOREIGN PATENT DOCUMENTS

WO    2008011725 A1    1/2008
WO    2008130634 A1   10/2008

OTHER PUBLICATIONS

Wang et al., "Arc-Modulated Radiation Therapy (AMRT): A Single Arc Form of Intensity-Modulated Arc Therapy," Physics in Medicine and Biology 53 (2008); 13 pages; IOP Publishing.
Xing et al., "Fast Iterative Algorithms for Three-Dimensional Inverse Treatment Planning," Medical Physics, Oct. 1998, pp. 1845-1849, vol. 25 (10); American Association of Physicists in Medicine, U.S., 5 pages.
Siebers et al., "Acceleration of dose calculations for intensity-modulated radiotherapy," Medical Physics, Jun. 2001, pp. 903-910, vol. 28 (6); American Association of Physicists in Medicine, U.S. 8 pages.
Djajaputra et al., "Algorithms and performance of a clinical IMRT Beam-Angle Optimization System," Phy. Med. Bio. 2003; vol. 48, pp. 3191-3212.
PCT Search Report from related PCT/EP2010/052156; dated May 5, 2010, 14 pages.

* cited by examiner

APPARATUS AND METHOD TO FACILITATE ADAPTING A RADIATION TREATMENT PLAN

RELATED APPLICATION(S)

This application is related to co-pending and co-owned U.S. patent application Ser. No. 11/954,638, entitled TREATMENT PLANNING SYSTEM AND METHOD FOR RADIOTHERAPY and filed Dec. 12, 2007, which is incorporated by reference in its entirety herein (including specifically the various definitions and word/expression characterizations contained therein).

TECHNICAL FIELD

This invention relates generally to radiation therapy treatment plans and more particularly to the optimization of such plans.

BACKGROUND

Radiation therapy techniques using radiation comprised of photons or particles such as electrons, protons, or heavier particles are known. Generally speaking, a trained person such as a radiologist, a radiation oncologist, or the like treats a patient having undesired tissue (such as a tumor) by irradiating the undesired tissue in order to reduce or eradicate that undesired tissue. As such treatment can also damage or destroy healthy tissue, such radiation is typically administered in accordance with a corresponding plan. The goal of such a plan is usually to control the shape, strength, timing, and other characterizing attributes of the radiation beam (or beams) to limit the effects of the radiation to only the undesired tissue.

The development of such a plan comprises a complicated and often dynamic undertaking. Such a plan will ordinarily need to account for both the general geometries and characteristics of a given radiation platform as well as the unique attributes or capabilities of a given specific radiation platform to be employed in a given treatment scenario. Such a plan will also often heavily depend upon information regarding the undesired tissue itself as well as desired tissue in the vicinity of the former. This can include, for example, information concerning the treatment volume itself (such as the size and shape of the treatment volume) as well as relative positioning of that treatment volume with respect to other adjacent desired tissue.

To meet these needs, it is known, for example, to employ algorithmic and multiple-algorithm processes to calculate and devise an optimum specific, three-dimensional treatment plan for irradiating a given treatment volume in a given patient using a given irradiation platform through use of a variety of administration angles, power levels, and/or exposure times. Unfortunately, these treatment-planning processes are typically computationally intensive. In addition, many of the more useful processes are iterative in nature. As a result, it can be very time consuming to develop a useful radiation treatment plan for a given patient on a given day.

Such problems are exacerbated by the fact that most treatment plans require administration of a series of treatment fractions over a number of hours, days, weeks, or months. As these are highly dynamic application settings, however, virtually all of the pertinent parameters regarding the patient and the undesired tissue can and will change over time. These changes, in turn, may render an earlier calculated treatment plan less effective or even dangerous. This, in turn, leads to a need to re-calculate the plan to be observed for each treatment session.

To accommodate such circumstances, new (current) information regarding at least one physical characteristic regarding the patient is usually developed. This can comprise, for example, using imaging technology to obtain data regarding the undesired tissue and local desired tissue. An experienced human observer then studies this data to characterize this information in a form that is suitable for use in a treatment plan calculation process.

As already noted, however, the calculation of such plans is quite time consuming. The burdening of the time line to accommodate the human-assessed information upon which such a treatment plan adaptation process depends simply makes a bad situation worse in this regard. These corresponding delays can lead to patient discomfort and inconvenience as well as scheduling difficulties and unwanted platform downtime. Patient discomfort compounded by delay can in turn lead to unwanted movement by the patient resulting in an error in targeting and reduced treatment effectiveness.

BRIEF DESCRIPTION OF THE DRAWINGS

The above needs are at least partially met through provision of the method and apparatus to facilitate adapting a radiation treatment plan described in the following detailed description, particularly when studied in conjunction with the drawings, wherein.

Figure 1:
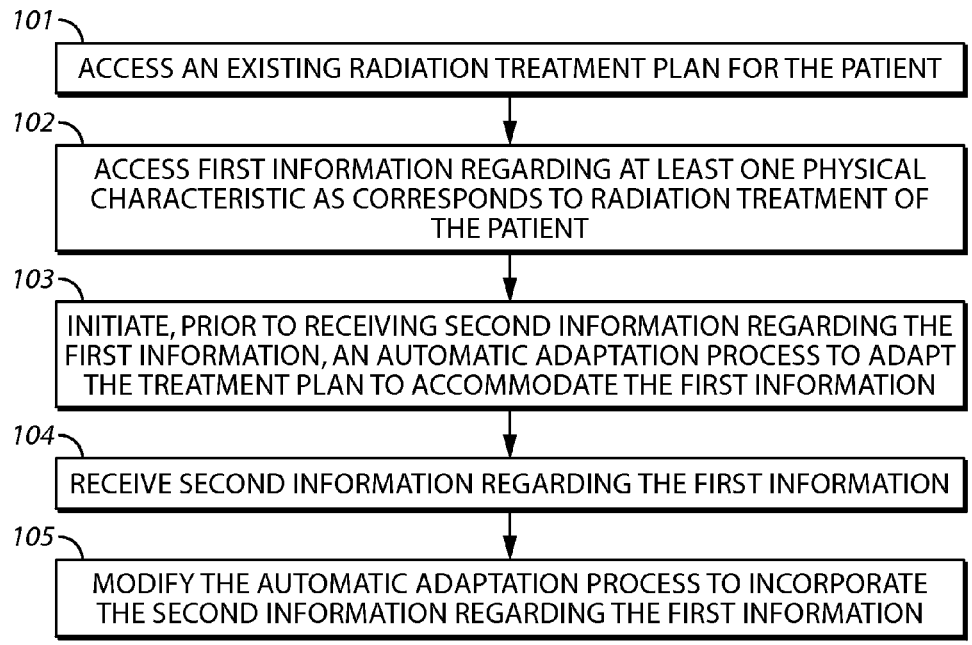
FIG. 1 comprises a flow diagram as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, one accesses both an existing radiation treatment plan for a given patient as well as first information (such as automatically generated updated information) regarding at least one physical characteristic as corresponds to the radiation treatment of this patient. One then initiates, prior to receiving second information (such as user input) regarding the updated information, an automatic adaptation process to adapt the treatment plan to accommodate the first information. Upon later receiving second information regarding the updated information, one then modifies the automatic adaptation process itself to incorporate the second information regarding the first information.

These teachings will readily accommodate using an already-implemented radiation treatment plan as the aforementioned existing radiation treatment plan. The aforementioned physical characteristic can vary with the application setting. Examples in this regard include, but are not limited to, information regarding biological structures in the patient (including, for example, a biological mass that is the intended treatment target of the treatment plan).

The aforementioned first information can also vary with the application setting. These teachings will readily accommodate, for example, using automatically generated imaging information in this regard. In such a case, the aforementioned second information can comprise correction information as corresponds to automatically interpreted information regarding the physical characteristic(s) of interest that is based upon the imaging information.

So configured, those skilled in the art will recognize and appreciate that these teachings permit a radiation treatment plan adaptation process to begin using existing treatment plan information coupled with automatically-derived current information regarding one or more physical characteristics of the patient. Later, while the process continues but after a human observer has had the opportunity to review the aforementioned current information regarding the patient's physical characteristic(s), the process can be updated, on the fly, to include such corrections as the human observer may feel are appropriate.

While it may seem counterintuitive to interrupt an algorithmic approach mid-process with data that is different than that with which the approach initially began, the applicant has determined that in many cases such an approach will in fact reduce the total amount of time required to identify a satisfactory treatment plan. This may be particularly true if for example changes introduced by an experienced observer are small in comparison to those corresponding to automatically generated updated information or if it takes a significant period of time for an experienced observer to conduct such a review. This reduction in overall time can, in turn, reduce the amount of time that a patient must wait between their pre-treatment imaging and the implementation of the treatment fraction to be delivered. This savings in time can lead to reduced patient fatigue, discomfort, and dissatisfaction while also tending to reduce treatment errors and downtime for the irradiating platform and corresponding personnel.

Those skilled in the art will recognize and appreciate that these benefits are likely achievable with a wide variety of treatment platforms and techniques and also with a wide variety of treatment plan determination processes and algorithms. It will further be appreciated that these benefits are attainable with little or no increased hardware requirements and with only a modest amount of relatively simple training for a limited number of personnel.

These and other benefits may become clearer upon making a thorough review and study of the following detailed description. Referring now to the drawings, and in particular to FIG. 1, an illustrative process that is compatible with many of these teachings will now be presented. The illustrated process 100 generally serves as an approach to adapt a treatment plan for irradiating a treatment volume within a given patient. This process can be employed in conjunction with any of a wide variety of treatment platforms.

This process 100 includes the step 101 of accessing an existing radiation treatment plan for the patient. This can comprise, for example, a radiation treatment plan that has already been implemented for this particular patient. This can comprise, for example, retrieving a previously determined treatment plan that was last used in a most recent radiation treatment for this patient. This can further comprise, for example, segmented volumes representative of a Planning Target Volume (PTV) and healthy Organs at Risk (OAR). Use of such segmented volumes in radiation therapy planning is well known to those skilled in the art and is commonly used in calculating Dose Volume Histograms (DVH) or other measures in evaluating a proposed treatment plan. These segmented volumes can for example be automatically generated from images such as computed tomography images using automatic segmentation. One such automatic segmentation device for example is the Smart Segmentation™ feature set embodied in the Eclipse™ treatment planning system developed and sold by Varian Medical Systems, Inc.

Another step 102 provides for accessing first information (such as, but not limited to, automatically generated updated information) regarding at least one physical characteristic as corresponds to radiation treatment of the patient. In many cases, this first information will comprise automatically generated imaging information as may have been formed using any of a variety of imaging methodologies such as, but not limited to, x-rays, computed tomography, magnetic resonance imaging, positron emission tomography, and so forth. This first information, for example and without intending any limitations in this regard, may comprise automatically generated updated segmented volumes including one or more of PTV and OAR-based content taken immediately prior to delivering a specific fraction of radiation therapy. As a further example, these segmented volumes can be automatically generated by using automatic segmentation as described above. Alternatively, and by way of yet another non-limiting example, these segmented volumes can be automatically generated using deformable registration. The relative position and shapes of such automatically updated segmented volumes can be significantly different than the corresponding segmented volumes used in the existing radiation treatment plan, due for example to variations in the patient's position, relative posture, weight, and physiological response to treatment.

As used herein, this reference to "automatically generated updated information" will be understood to refer to information that was developed, at least in substantial part, by an automaton such as corresponding computer software that is able to discern and identify particular structures contained in imaging information for the patient and to automatically extract characterizing information regarding such structures such as various dimensions, shapes, material properties, relative position, and so forth.

The aforementioned physical characteristic can comprise, for example, a biological structure within the patient such as, but not limited to, a biological mass of interest (such as the intended treatment target of the treatment plan). In such a case, this automatically generated updated information can comprise data regarding the presence, relative location, relative orientation, shape, and dimensions of a tumor that is the subject of the treatment plan. Various approaches are known in the art with respect to the automatic generation of such information. As these teachings are not overly sensitive to any particular selection in this regard, for the sake of brevity and the preservation of clarity, further elaboration in this regard will not be presented here.

Another step 103 provides for initiating, prior to receiving second information (such as, but not limited to, user input)

regarding the aforementioned first information, an automatic adaptation process to adapt the treatment plan to accommodate the first information. By one approach, this comprises initiating the process without receiving any information regarding the first information. By another approach, this could comprise initiating the process after having received some modicum of supplemental information regarding the first information, but nevertheless in the absence of a more complete vetting of that first information as would ordinarily be expected.

Various automatic adaptation processes are known in the art and include, for example, iterative adaptation processes including processes that comprise two or more iterative adaptation processes that differ from one another. Specific examples in this regard appear in the aforementioned TREATMENT PLANNING SYSTEM AND METHOD FOR RADIOTHERAPY patent application.

As used herein, this reference to "second information regarding the aforementioned first information" will be understood to include substantive user input that reflects or incorporates an experienced observer's corrections to automatically generated updated information (or an indication that no such corrections are required). As one example in this regard, the automatically generated updated information might comprise updated segmented volumes of one or more PTV and OAR as described above while the experienced observer subsequently determines that a more appropriate contour should be applied instead. In such a case, new contours (or corresponding edits) can comprise the aforementioned user input regarding the updated information. Alternatively, if the experienced observer determines upon review that the automatically generated updated information is correct and appropriate an indication of approval might comprise the aforementioned user input.

It will therefore be understood and appreciated that this process 100 can begin a treatment plan adaptation process using automatically generated data that may, in fact, prove to be inaccurate at least in part. Nevertheless, the applicant has determined that, at least in many cases, this automatically generated information will be sufficiently accurate to permit a useful head start on the adaptation process. This can be particularly so when the adaptation process comprises one or more iterative adaptation processes.

A subsequent step 104 then provides for later receiving second information (such as, but not limited to, user input) regarding the updated information. When the user has determined that automatically generated updated information as comprises the first information is, in fact, sufficiently accurate, this second information can comprise user input that simply comprises a corresponding indication in this regard. When the user has determined that one or more value or characterization as comprises the automatically generated updated information is inaccurate, however, this second information can comprise information to correct the automated interpretation of the updated information. To continue with the example provided above, for example, this could comprise receiving information to indicate corrected contours associated to a PTV or OAR based on a review performed by an experienced observer.

Those skilled in the art will recognize and appreciate that this process 100 contemplates receiving this second information regarding the first information even as the automatic adaptation process of choice is working to provide a corresponding solution. As one simple illustrative example in this regard, the automatic adaptation process might be expected to utilize around thirty minutes to yield a treatment plan solution and it may typically require fifteen minutes for the experienced observer to assess updated information for the patient and make their determinations regarding the accuracy of automatically extracted values and characterizations. In such a case, the second information comprising user input regarding the updated information would be received about halfway through the overall adaptation determination process.

Accordingly, this process 100 also provides the step 105 of modifying the automatic adaptation process to incorporate the second information regarding the first information. As alluded to above, this can readily comprise modifying, during execution of the adaptation process, the treatment plan data that is being processed by that adaptation process.

When the corrections being input by the end user are relatively significant, it is possible that concluding the adaptation process might be considerably delayed. In many (if not most) cases, however, it is expected that these corrections will tend to be relatively minor. In such cases, it is expected that the processing window will not be noticeably increased. In these cases, then, those skilled in the art will recognize that the overall time required between obtaining the updated information for the patient and expressing an adapted treatment plan can be effectively reduced by the amount of time that would have ordinarily been associated with the experience observer's personal review of the updated information for that patient. In the simple example provided, this would mean a savings of fifteen minutes, or about one third of the overall previous required time to accommodate these steps.

Figure 2:
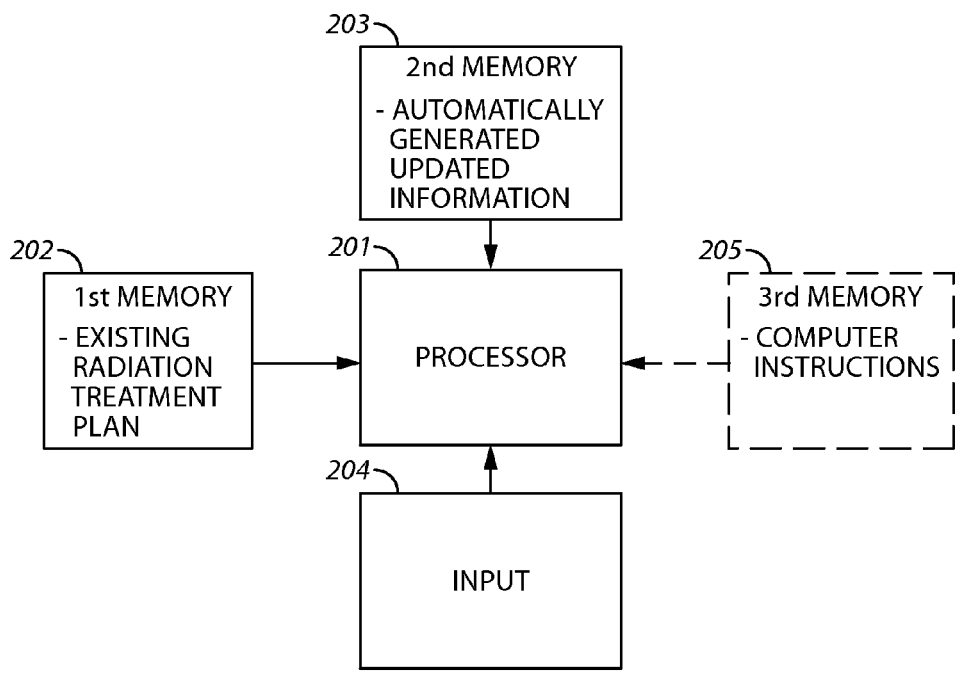
FIG. 2 comprises a block diagram as configured in accordance with various embodiments of the invention.

Those skilled in the art will appreciate that the above-described processes are readily enabled using any of a wide variety of available and/or readily configured platforms, including partially or wholly programmable platforms as are known in the art or dedicated purpose platforms as may be desired for some applications. Referring now to FIG. 2, an illustrative approach to such a platform will now be provided.

In this illustrative embodiment, the enabling platform comprises a processor 201 that operably couples to a first memory 202, a second memory 203, and an input 204. Those skilled in the art will recognize and appreciate that such a processor 201 can comprise a fixed-purpose hard-wired platform or can comprise a partially or wholly programmable platform. All of these architectural options are well known and understood in the art and require no further description here.

This first memory 202 can have stored therein an existing radiation treatment plan for irradiating a treatment volume with a given patient as described above. The second memory 203, in turn, can have stored therein the aforementioned automatically generated updated information regarding at least one physical characteristic as corresponds to the radiation treatment of the patient. Those skilled in the art will recognize that this illustration can be taken at face value (such that the first and second memories 202 and 203 comprise physically discrete components) or can serve as a logical representation (in which case, the first and second memories 202 and 203 can comprise portions of a fully or partially shared memory component) as desired. It will also be understood that the described contents can be distributed, if desired, over a plurality of memory components.

The input 204, of course, can serve as the interface by which the aforementioned user enters correction information regarding the automatically generated updated information as described above.

As suggested above, the processor 201 can be configured (via, for example, corresponding programming as will be well recognized and understood by those skilled in the art) to carry out one or more of the steps, actions, and/or functionalities as are set forth herein. This can comprise, for example, configuring the processor 201 to initiate, prior to receiving user input regarding the aforementioned updated information, an automatic adaptation process of choice to adapt a treatment plan to accommodate the updated information, receiving user input via the input 204 regarding the updated information, and then modifying the automatic adaptation process to incorporate the user input regarding that updated information. By one approach, if desired, computer instructions in these regards can optionally be stored in a storage medium such as a third memory 205.

Those skilled in the art will recognize and understand that such an apparatus may be comprised of a plurality of physically distinct elements as is suggested by the illustration shown in FIG. 2. It is also possible, however, to view this illustration as comprising a logical view, in which case one or more of these elements can be enabled and realized via a shared platform. It will also be understood that such a shared platform may comprise a wholly or at least partially programmable platform as are known in the art.

It is a given that modern radiation treatment plans require considerable time to develop and it is also a given that at least some of the physical parameters that such a plan must take into account change over an extended course of treatment. It is an unfortunate circumstance that patients are necessarily subjected to enduring lengthy waits between when the examinations are made to identify changes with respect to their physical circumstances and when a corresponding adapted plan becomes available to implement. Those skilled in the art will recognize and appreciate that these teachings can lead to a considerable reduction with respect to this delay. It will also be appreciated that these teachings are readily applied in conjunction with essentially any presently available processes to adapt such a treatment plan.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method of adapting a treatment plan for irradiating a treatment volume within a patient, comprising:
    accessing an existing radiation treatment plan for the patient;
    accessing first information for the patient that comprises automatically generated segmented volumes representing at least one of a planning target volume (PTV) and a healthy organ at risk (OAR);
    subsequent to accessing the existing radiation treatment plan and the first information, initiating an automatic adaptation process to adapt the treatment plan to accommodate the first information;
    subsequent to initiating the automatic adaptation process and prior to the automatic adaptation process yielding a treatment plan solution, receiving second information regarding the first information, wherein the second information includes input comprising an experienced observer's corrections to at least one volume contour for at least one PTV or OAR contained in the first information; and
    prior to the automatic adaptation process yielding a treatment plan solution, modifying the automatic adaptation process to incorporate the second information regarding the first information.

2. The method of claim 1 wherein accessing the existing radiation treatment plan for the patient comprises accessing an already-implemented radiation treatment plan for the patient.

3. The method of claim 1 wherein accessing first information comprises accessing automatically generated updated information.

4. The method of claim 3 wherein accessing automatically generated updated information comprises, at least in part, accessing automatically generated updated segmented volumes.

5. The method of claim 4 wherein accessing automatically generated updated segmented volumes comprises, at least in part, accessing automatically generated updated segmented volumes representative of at least one of a Planning Target Volume (PTV) and healthy Organs at Risk (OAR) content.

6. The method of claim 4 wherein accessing automatically generated updated segmented volumes comprises, at least in part, accessing automatically generated updated segmented volumes generated by using automatic segmentation.

7. The method of claim 4 wherein accessing automatically generated updated segmented volumes comprises, at least in part, accessing automatically generated updated segmented volumes generated by using deformable registration.

8. The method of claim 1 wherein the automatic adaptation processes comprises an iterative adaptation process.

9. The method of claim 8 wherein the automatic adaptation processes comprises at least two iterative adaptation processes that differ from one another.

10. The method of claim 1 wherein the second information regarding the first information comprises information to correct an automated interpretation of the first information.

11. The method of claim 10 wherein modifying the automatic adaptation process to incorporate the second information comprises modifying, during execution of the adaptation process, treatment plan data being processed by the adaptation process.

12. An apparatus comprising:
    a first memory having stored therein an existing radiation treatment plan for irradiating a treatment volume within a patient;
    a second memory having stored therein first information for the patient comprising automatically generated segmented volumes representing at least one of a planning target volume (PTV) and a healthy organ at risk (OAR);
    an input;
    a processor operably coupled to the first memory, the second memory, and the input and being configured to:
        initiate an automatic adaptation process to adapt the treatment plan to accommodate the first information;
        subsequent to initiating the automatic adaptation process and prior to the automatic adaptation process yielding a treatment plan solution, receive second information via the input regarding the first information, wherein the second information comprises an experienced observer's corrections to at least one volume contour for at least one PTV or OAR contained in the first information; and
        prior to the automatic adaptation process yielding a treatment plan solution modify the automatic adaptation process to incorporate the second information regarding the first information.

13. The apparatus of claim 12 wherein the existing radiation treatment plan for the patient comprises an already-implemented radiation treatment plan for the patient.

14. The apparatus of claim 12 wherein the automatic adaptation processes comprises an iterative adaptation process.

15. The apparatus of claim 12 wherein the second information regarding the first information comprises information to correct an automated interpretation of the first information.

16. An apparatus comprising:
a storage medium having stored therein a set of computer instructions for:
  accessing an existing radiation treatment plan for a patient;
  accessing first information for the patient comprising automatically generated segmented volumes representing at least one of a planning target volume (PTV) and a healthy organ at risk (OAR);
  initiating, prior to receiving second information regarding the first information, an automatic adaptation process to adapt the treatment plan to accommodate the first information;
  prior to the automatic adaptation process yielding a treatment plan solution receiving second information regarding the first information wherein the second information comprises an experienced observer's corrections to at least one volume contour for at least one PTV or OAR contained in the first information; and
  prior to the automatic adaptation process yielding a treatment plan solution modifying the automatic adaptation process to incorporate the second information regarding the first information.

17. The apparatus of claim 16 wherein accessing first information comprises accessing automatically generated updated information.

18. The apparatus of claim 17 wherein accessing automatically generated updated information comprises, at least in part, accessing automatically generated updated segmented volumes.

19. The apparatus of claim 18 wherein accessing automatically generated updated segmented volumes comprises, at least in part, accessing automatically generated updated segmented volumes representative of at least one of a Planning Target Volume (PTV) and healthy Organs at Risk (OAR) content.

20. The apparatus of claim 18 wherein accessing automatically generated updated segmented volumes comprises, at least in part, accessing automatically generated updated segmented volumes generated by using automatic segmentation.

21. The apparatus of claim 18 wherein accessing automatically generated updated segmented volumes comprises, at least in part, accessing automatically generated updated segmented volumes generated by using deformable registration.

22. The apparatus of claim 16 wherein the automatic adaptation processes comprises an iterative adaptation process.

23. The apparatus of claim 22 wherein the automatic adaptation processes comprises at least two iterative adaptation processes that differ from one another.

24. The apparatus of claim 16 wherein the second information regarding the first information comprises information to correct an automated interpretation of the first information.

25. The apparatus of claim 24 wherein modifying the automatic adaptation process to incorporate the second information comprises modifying, during execution of the adaptation process, treatment plan data being processed by the adaptation process.

* * * * *